US00PP34190P2

(12) United States Plant Patent
Bagdasarian et al.

(10) Patent No.: US PP34,190 P2
(45) Date of Patent: May 3, 2022

(54) STRAWBERRY PLANT NAMED 'MISS JO'

(50) Latin Name: ***Fragaria* x *ananassa***
Varietal Denomination: Miss Jo

(71) Applicants: Jimmy Haig Bagdasarian, Santa Cruz, CA (US); Nicholas Jack Pinkerton, Redding, CA (US); Travis Stegmeir, Salinas, CA (US)

(72) Inventors: Jimmy Haig Bagdasarian, Santa Cruz, CA (US); Nicholas Jack Pinkerton, Redding, CA (US); Travis Stegmeir, Salinas, CA (US)

(73) Assignee: Lassen Canyon Nursery, Inc., Redding, CA (US)

( * ) Notice: Subject to any disclaimer, the term of this patent is extended or adjusted under 35 U.S.C. 154(b) by 0 days.

(21) Appl. No.: 17/447,437

(22) Filed: Sep. 12, 2021

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./208, 209
CPC ..... A01H 5/0893
See application file for complete search history.

(56) References Cited

U.S. PATENT DOCUMENTS

| | | | |
|---|---|---|---|
| PP26,974 | P3 | 7/2016 | Bagdasarian |
| PP27,034 | P3 | 8/2016 | Bagdasarian |
| PP27,190 | P3 | 9/2016 | Bagdasarian |
| PP30,326 | P2 | 4/2019 | Bagdasarian |
| PP30,426 | P2 | 4/2019 | Bagdasarian |
| PP30,427 | P2 | 4/2019 | Bagdasarian |
| PP33,284 | P2 | 7/2021 | Bagdasarian |

*Primary Examiner* — Kent L Bell
(74) *Attorney, Agent, or Firm* — Phase M Legal

(57) ABSTRACT

A new and distinct variety of strawberry plant (*Fragaria* x *ananassa*) named 'Miss Jo' is presented here. This new weak day neutral strawberry variety is characterized by moderately high vigor plants which produce attractive conical fruit with a good, sweet strawberry flavor and a desirable lighter red exterior color. The variety is fully remontant in cool coastal areas of California, producing high quality fruit all season long.

7 Drawing Sheets

Latin name of the genus and species of the plant claimed: Botanical classification: *Fragaria* x *ananassa.*

Variety denomination: The new strawberry variety denomination is 'Miss Jo'.

BACKGROUND OF THE INVENTION

Field of Invention

The present invention relates to a new and distinct variety of strawberry named 'Miss Jo'. This new weak day neutral strawberry variety is the result of a controlled cross in an ongoing breeding program made in 2014. Jimmy Bagdasarian, Nicholas Pinkerton, and Travis Stegmeir are the co-inventors. The variety is botanically known as *Fragaria* x *ananassa.*

The primary market for the 'Miss Jo' variety is for the fresh market sales of the fruit. 'Miss Jo' produces high quality, medium to large firm berries, which are attractive, and which have good flavor. The variety 'Miss Jo' is a weak day neutral variety, allowing for an extended season of fruit.

Comparison with Parent Varieties

The new variety 'Miss Jo' resulted from a controlled cross conducted in an ongoing breeding program between a strawberry variety designated '22G22', (unpatented), and a strawberry variety designated '52L32', (unpatented). The female parent, '22G22', is a short-day variety characterized by a compact, dense plant, and shorter conic, dark, high-gloss fruit. The fruit have good flavor, and '22G22' is considered completely remontant in coastal areas of cooler temperatures. The male pollen parent '52L32' is day neutral plant, characterized by its large, firm long conical fruit which have a light red exterior and interior color, and low gloss. Plants of '52L32' ate of medium vigor.

The aforementioned controlled cross was carried out in a breeding program at Santa Cruz, Calif., USA. Pollen taken from an '22G22' plant pollinated a female '52L32' plant. The flowers were covered so that no other pollen could contaminate the procedure.

Strawberries developed, were later harvested and the seeds resulting from this cross were extracted and germinated in a greenhouse at Redding, Calif., USA. The resulting seedlings were then transplanted to Shastina, Calif. in 2015, grown for an additional period and allowed to propagate asexually via stolens. Plants were then harvested and planted in breeding test plots in late September in: Oxnard, Calif. (Ventura County); and late October/early November in Watsonville, Calif. (Monterey County). The selection of the new variety was first made in Oxnard, Calif., and designated '146T54' in 2015. This selection was later named 'Miss Jo'.

The new variety was further propagated asexually by stolens in breeding plots in: Macdoel, Calif. (Siskiyou County); and Manteca, Calif. (San Joaquin County). The new variety has also been "meristemed." Small pieces of plant material (approximately 0.5 mm in diameter), consisting of the undifferentiated meristem tissue and one or two leaf primordia, were removed from the buds on crowns of young daughter plants, then placed on nutrient medium, and new plants were grown from them. Planting stock from the "meristemed" plants are growing in a screenhouse located in Redding, Calif.

The propagules of 'Miss Jo' ('146T54') are identical to the original plant in all distinguishing characteristics; accordingly, the propagation has demonstrated that the traits disclosed herein remain fixed and true to type through successive generations of asexual reproduction.

SUMMARY OF THE INVENTION

'Miss Jo' is a weak day neutral variety exhibiting the following combination of characteristics, which have been observed repeatedly, and which distinguish this strawberry plant as a new and distinct variety:

1. The variety produces moderate sized fruit;
2. The fruit is generally well shaped conical;
3. The fruit is attractive, having a glossy light red exterior and interior;
4. The fruit is sweet tasting, with good flavor;
5. The variety produces a high volume of marketable fruit;
6. The plants of the variety are of moderate to high vigor; and,
7. The variety has shown rain tolerance in wet climates.

'Miss Jo' fruit demonstrates characteristics and qualities that are desired by fresh market strawberry sales companies. The lighter, red color is preferred by many shippers of fresh strawberries, as the darker berries are more likely to be viewed as overripe by buyers then are lighter colored berries. 'Miss Jo' is also a firm berry, which should lend well to a fresh market where shipping is a major factor. The vigor and density of 'Miss Jo' plants are moderately high, with flowers that are at, or extend slightly over the canopy, allowing for adequate pollination. Fruit is easily seen and accessible on the shoulders of the beds allowing for ease of picking.

BRIEF DESCRIPTION OF THE DRAWINGS

The accompanying color photographs, identified as FIGS. 1 through 7, show the appearance of typical specimens of the new strawberry variety, initially designated '146T54', and now named 'Miss Jo'. These Figures depict the colors, as nearly true as it is reasonably possible given differences in color illustrations of this character. Accordingly, color in the photographs may differ slightly from the colors discussed in the botanical description. The photographs of the depicted plant, plant parts, and fruit of 'Miss Jo' were taken in June 2021.

DETAILED BOTANICAL DESCRIPTION OF THE PLANT

Figure 1:
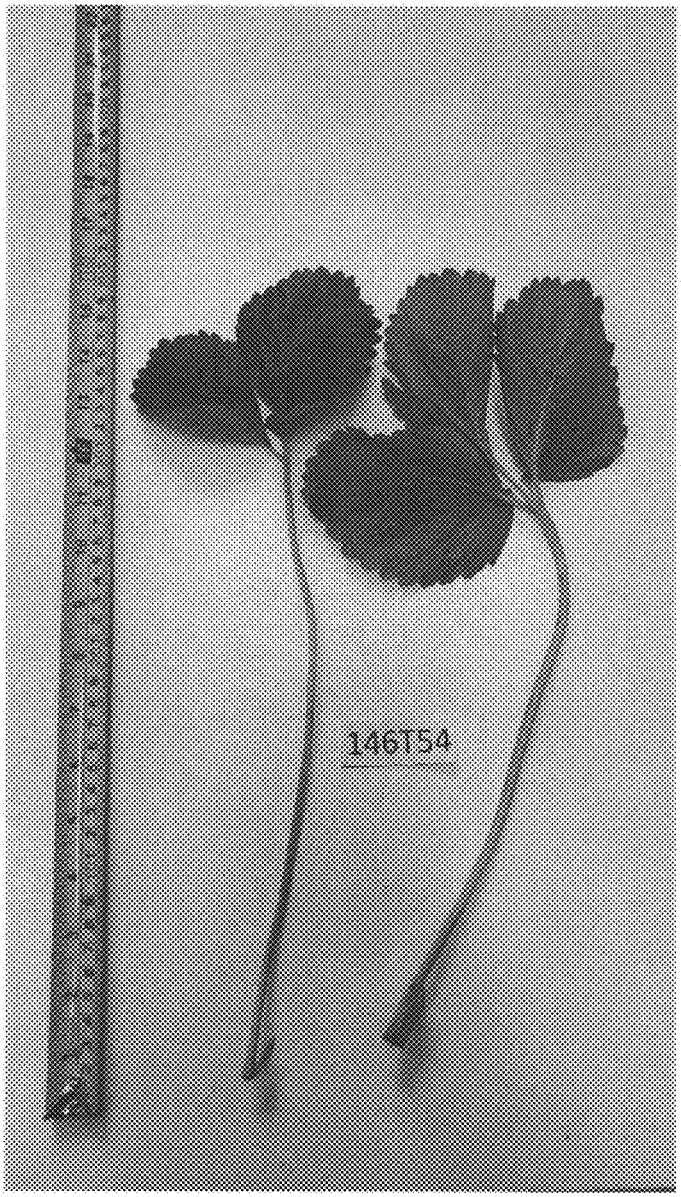
FIG. 1 shows typical leaf and petiole structure at mid-season.
Figure 2:
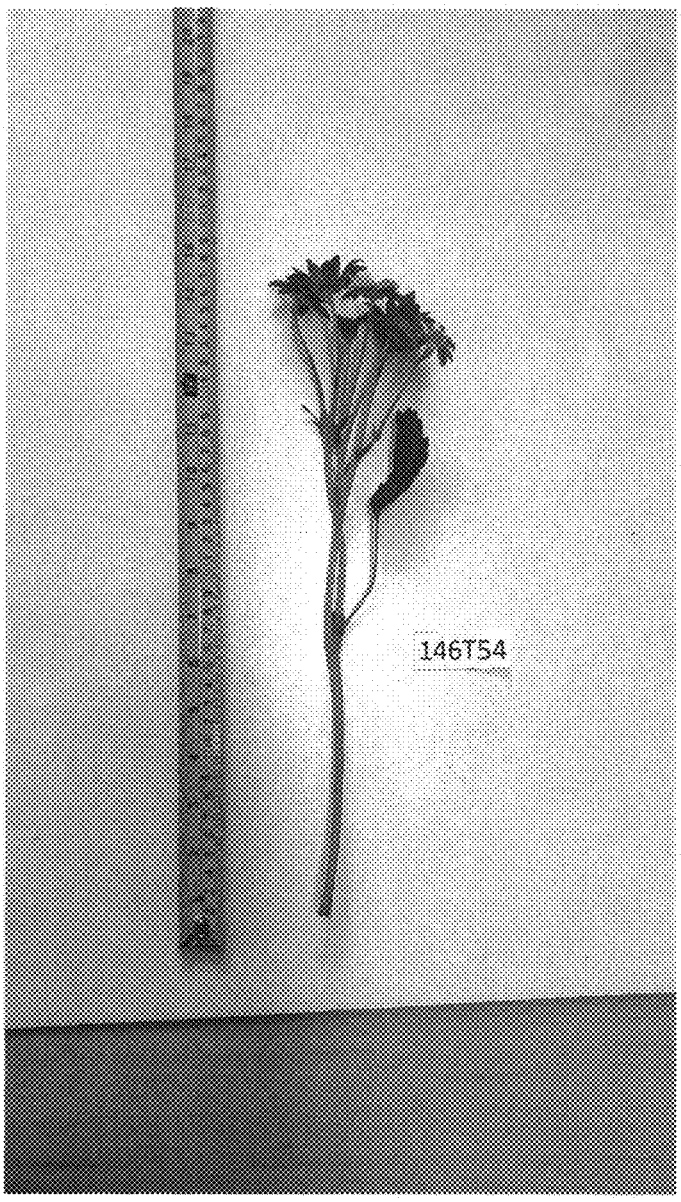
FIG. 2 shows an inflorescence at mid-season.
Figure 3:
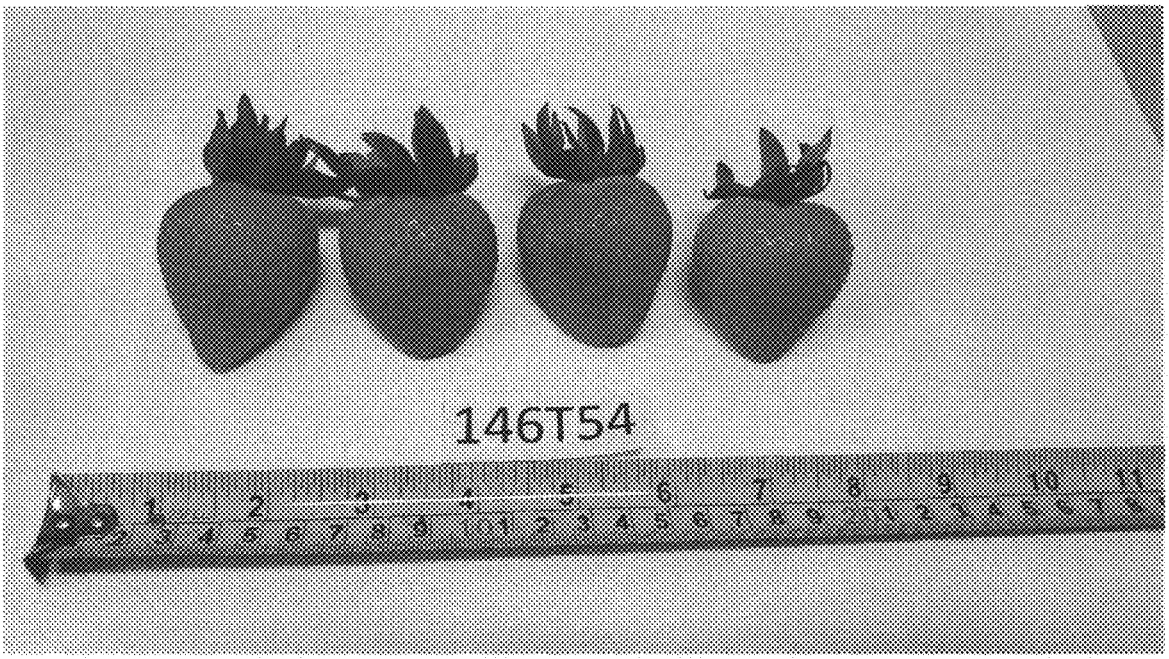
FIG. 3 shows a selection of typical mid-season fruit.
Figure 4:
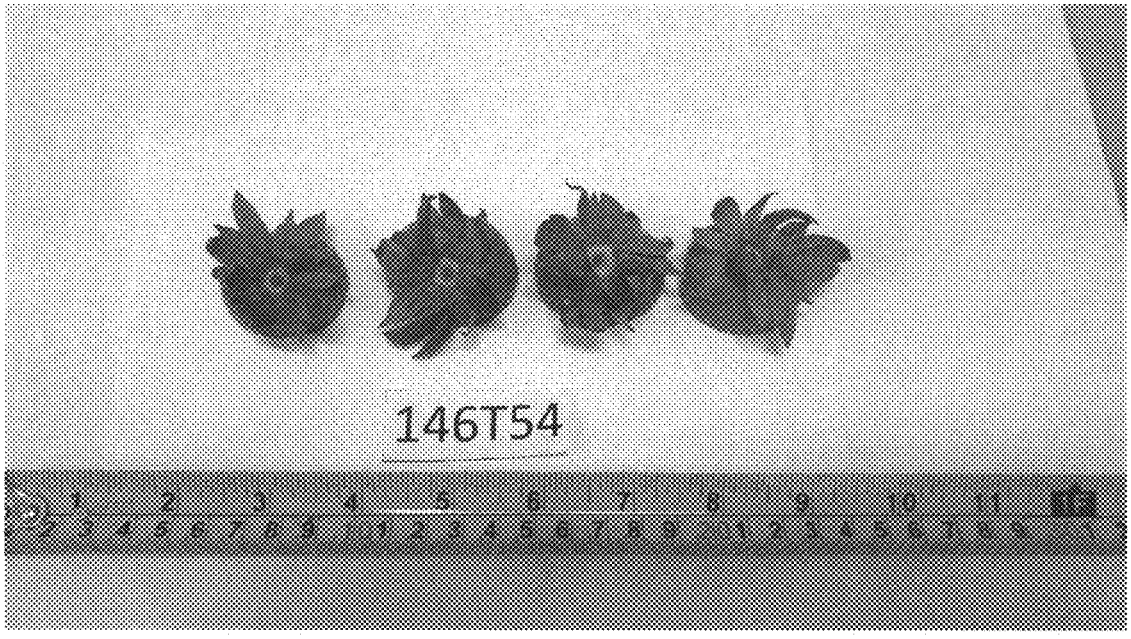
FIG. 4 shows typical calyx position over the berry of 'Miss Jo'.
Figure 5:
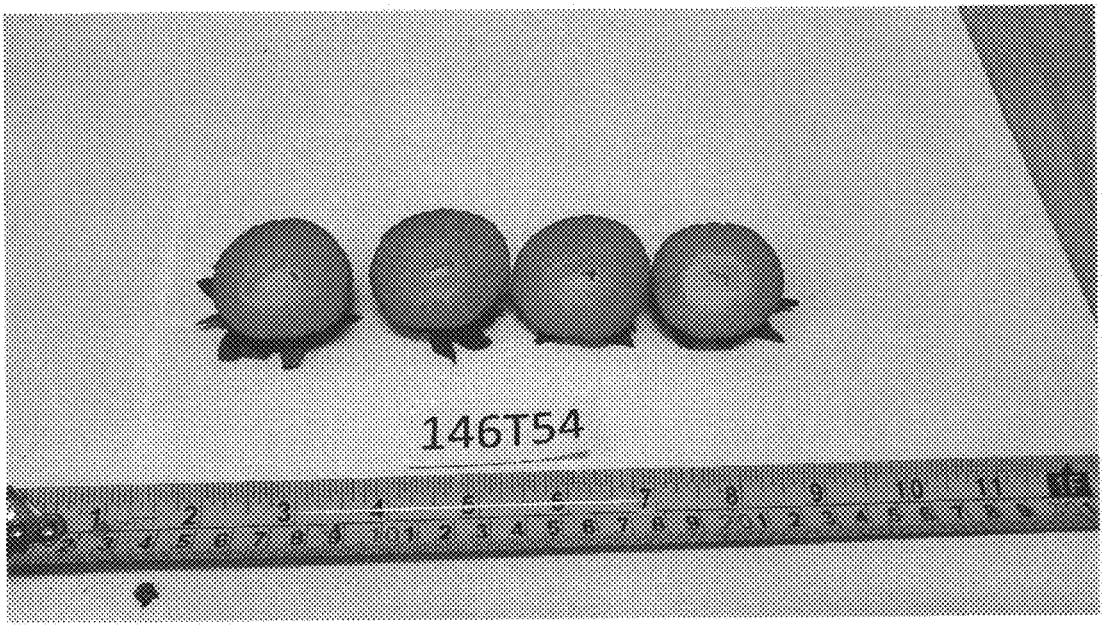
FIG. 5 shows a cross-section of typical fruit internal coloration and core size.
Figure 6:
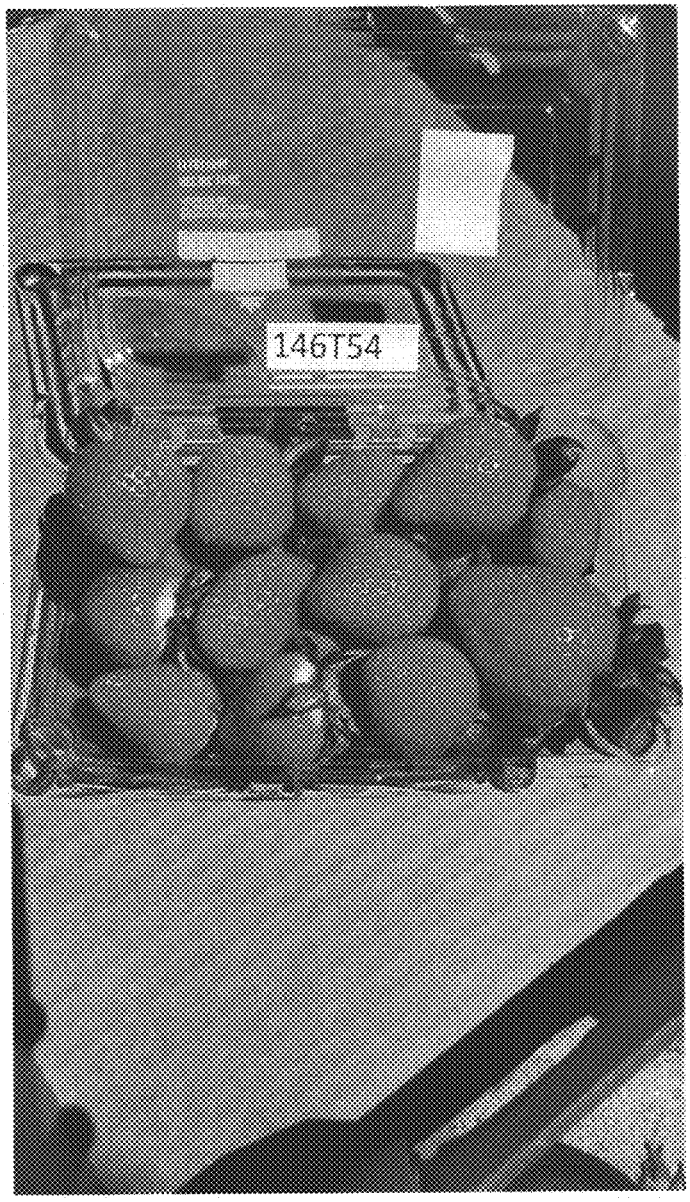
FIG. 6 shows a container of freshly picked fruit.
Figure 7:
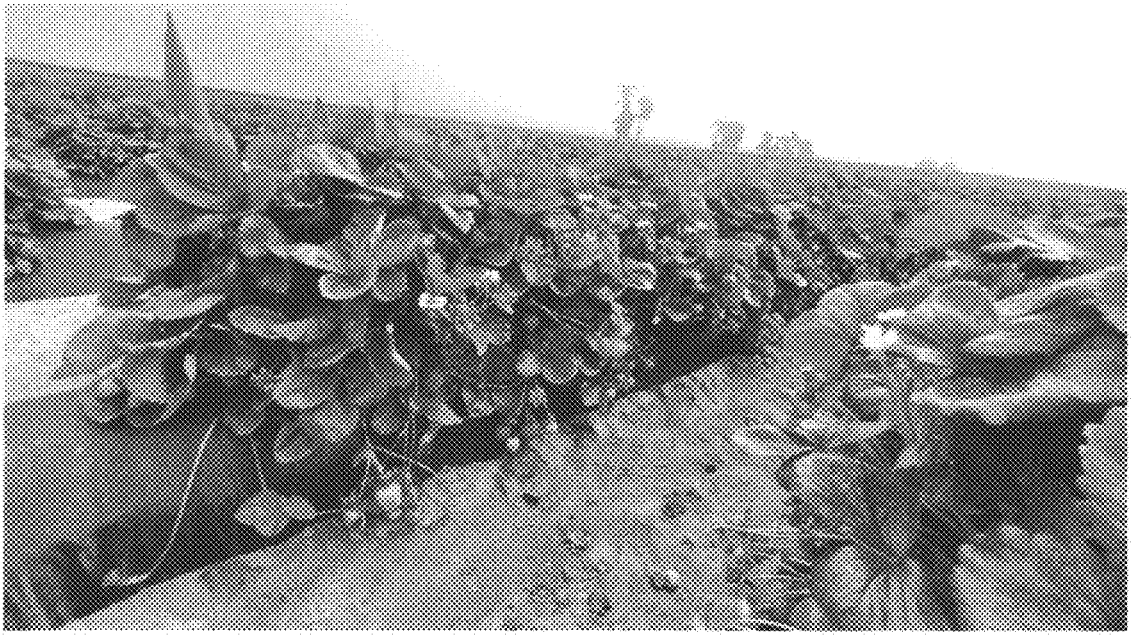
FIG. 7 shows typical plants in a field and position of ripe fruit on the shoulder.

'Miss Jo' is a new and distinct variety of strawberry, genus and species *Fragaria* x *ananassa*. It is the result of a cross between its female parent, '22G22' (unpatented), and its male parent '52L32' (unpatented). '22G22' is a short-day variety, while '52L32' is a day neutral variety. 'Miss Jo' is a weak day neutral variety that has remontant or ever-bearing tendencies in temperate coastal environments and is partially remontant in hotter inland environments. Plants of 'Miss Jo' bloom commonly in our high elevation nursery, and slightly in the heat of our low elevation nursery location in Manteca, Calif., consistent with other weak day neutral varieties. The plants of the new variety have a moderately high vigor and produce multiple crowns during the growing season. 'Miss Jo' exhibits several characteristics which are improvements over one or both of its parent varieties, and other known cultivars. The characteristics of 'Miss Jo' were observed in plants aged about 6 months from planting in fruiting fields. These characteristics and comparisons with other cultivars are discussed following.

The fruit size of 'Miss Jo' is large, with a seasonal average of 26 g, slightly smaller than its parents. The size of fruit of 'Miss Jo' is ideal where it is not too large where it could be damaged in containers, but not too small to allow for efficient picking and packing. The fruit of 'Miss Jo' also hangs down on the shoulder of the bed to allow for more visible fruit and ease of picking.

'Miss Jo' produces mostly short conic fruit like its parent '22G22', while the fruit of '52L32' is a longer conical shape, often with mis-shaped fruit. The fruit of 'Miss Jo' generally ripens evenly from the tip to the shoulders of the berry, resulting in a uniform light red color over the whole fruit. In contrast, the fruit of '52L32' has a more pronounced tip to top ripening pattern that can often be blotchy. The fruit of 'Miss Jo' is mostly absent of creases and is generally smooth and has a firmness that is equal to its two parents. The glossiness of 'Miss Jo' is closer to that of its '22G22' parent which has a high gloss, rather than the lower gloss of '52L32'.

The data set forth for 'Miss Jo' in Tables 1, 2, and 3 was collected in June 2021 from plants grown at a test plot in Moss Landing, Monterey County, Calif. Yield, size and % Brix data was used from the previous season (2020) at the same location. Color terminology where noted is in accordance with the Pantone Color Formula Guide GP 1201.

In Table 1, the observed characteristics of 'Miss Jo' are set forth.

TABLE 1

Detailed Description of Characteristics of 'Miss Jo'

| | |
|---|---|
| SPECIFICATION: | |
| Genus/Species | *Fragaria* X *ananassa* |
| Market Name | Strawberry |
| PARENTS: | |
| Female | '22G22' (unpatented) |
| Male | '52L32' (unpatented) |
| PLANT: | |
| Type | Weak Day Neutral |
| Growth Habit | Upright |
| Foliage density | Moderate/High |
| Vigor | Moderate/High |
| Height | Average 36 cm; range 33 cm to 40 cm |
| Width | Average 54.2 cm; range 50 cm to 60 cm |
| Crowns | Multiple crowns produced throughout season |
| Disease tolerance | Test plots have shown tolerance to Fusarium and Anthracnose |

TABLE 1-continued

| Detailed Description of Characteristics of 'Miss Jo' | |
|---|---|
| LEAF: | |
| Width | Average 15.6 cm; range 13.5 cm to 18 cm |
| Color | Adaxial surface: Pantone 371 U<br>Abaxial surface: Pantone 7491 U |
| Pubescence | Medium density |
| Inter-vein blistering | Slight |
| Glossiness | Moderate |
| Variegation | None |
| TERMINAL LEAFLET: | |
| Length | Average 94.8 mm; range 76 mm to 108 mm |
| Width | Average 81.6 mm; range 69 mm to 95 mm |
| Ratio Length to width | 1.16 |
| Margins | Crenate to serrate |
| Leaflet shape | Obovate |
| Base shape | Cuneate |
| Cross-section shape | Concave |
| PETIOLE: | |
| Pubescence | Slight |
| Petiole color | Pantone 383 U |
| Petiole length | Average 26.7 cm; range 23.2 cm to 29.1 cm |
| Petiole diameter | Average 4.05 mm; range 3.42 mm to 4.81 mm |
| STIPULE: | |
| Anthocyanin coloration | Slight |
| Length | Average 21.96 mm; range 19.92 mm to 24.58 mm |
| Width | Average 11.23 mm; range 9.36 mm to 13.22 mm |
| STOLEN: | |
| Anthocyanin coloration | Present, light |
| Pubescence | Moderate, fine |
| Diameter | Average 4.31 mm; range 3.03 mm to 5.82 mm |
| INFLORESCENCE: | |
| Flowering time | Moderately early |
| Position | At or slightly above the canopy |
| Number of blooms | Average 6.4; range 5 to 9 |
| Length | Average 37.2 cm; range 32.9 cm to 43.5 cm |
| Flower diameter | Average 26.6 mm; range 21.9 mm to 30.2 mm |
| Petal arrangement | Separate to slightly overlapping |
| Petal number | Average 5.6; range 5 to 8 |
| Petal length | Average 11.4 mm; range 10.2 mm to 12.51 mm |
| Petal width | Average 10.8 mm; range 9.23 mm to 12.15 mm |
| Ratio Length to width | 1.05 |
| Petal color | Pantone 11-0701 TPX |
| Calyx | Larger than the corolla |
| Calyx color | Adaxial Pantone 371 U<br>Abaxial Pantone 3791 U |
| Stamens | Average 27.5; range 26 to 34 |
| Pedicel | Attitude of hairs is perpendicular to upright |
| FRUIT: | |
| Bearing | Weak Day Neutral |
| Shape | Conic |
| Size | Seasonal average: 26 g |
| Achenes | Slightly below the surface |
| Glossiness | Medium |
| External color | Pantone 711 C |
| Internal color | Pantone 7417 C |
| Evenness of external color | Even |
| Width of band at top devoid of achenes | Small |
| Yield | Approximate grams per plant: 1,926 g |
| Firmness | Firm, similar firmness to parent '22G22' |
| % Brix | Seasonal average: 8.9; range 6.7 to 12.2 |

The comparison statistics set forth in the following Tables are with respect to characteristics observed at mid-season of 'Miss Jo'. All measurements for 'Miss Jo' were taken at a test plot in Moss Landing, Monterey County, Calif. during mid-season 2021. In Tables 2 and 3, the characteristics of 'Miss Jo' are compared with historical data of the day neutral variety 'Sweet Ann' (U.S. Plant Pat. No. 22,472) and short-day variety 'Lucia' (U.S. Plant Pat. No. 26,974). Color identifications where noted herein are in accordance with the Pantone Color Formula Guide.

PLANTS AND FOLIAGE

The form and structure of the plants of 'Miss Jo' are slightly shorter to that of 'Lucia' and 'Sweet Ann' plants. The plant spread of 'Miss Jo', however, is wider than that of either 'Sweet Ann' or 'Lucia'. The canopy of 'Miss Jo' is slightly denser than that of 'Sweet Ann' and 'Lucia'. The leaf surface of 'Miss Jo' is also less blistered than that of 'Lucia' and more closely resembling that of 'Sweet Ann'. The glossiness of the leaves of 'Miss Jo' is also less glossy than that of 'Lucia' and more like that of 'Sweet Ann'.

In Table 2, comparative data for foliar characteristics are presented for 'Miss Jo' and historical data of two comparison cultivars, 'Sweet Ann' and 'Lucia'.

TABLE 2

Foliar Characteristics of 'Miss Jo' Compared to 'Lucia' and 'Sweet Ann'

| Foliar Characteristics | | Cultivar 'Lucia' | 'Sweet Ann' | 'Miss Jo' |
|---|---|---|---|---|
| Plant height (mm) | Average | 391 | 380 | 360 |
| | Range | 292-490 | 290-480 | 330-400 |
| Plant spread (mm) | Average | 472 | 420 | 542 |
| | Range | 430-550 | 30-510 | 500-600 |
| Leaf width (mm) | Average | 195 | 165 | 156 |
| | Range | 165-220 | 130-195 | 135-180 |
| Mid-tier leaflet length (mm) | Average | 103 | 88 | 94.8 |
| | Range | 82-116 | 72-105 | 76-108 |
| Mid-tier leaflet width (mm) | Average | 91 | 67 | 81.6 |
| | Range | 73-102 | 52-88 | 69-95 |
| Petiole length (mm) | Average | 268 | 220 | 267 |
| | Range | 230-355 | 150-280 | 232-291 |
| Petiole diameter (mm) | Average | 4.48 | 3.74 | 4.05 |
| | Range | 3.70-5.80 | 3.01-4.29 | 3.42-4.81 |
| Number leaflets per leaf | | 3 | 3 | 3 |
| Leaf convexity | | Slight concave | Slight concave | Concave |
| Shape leaflet base | | Rounded to obtuse | Obtuse | Cuneate |
| Leaf pubescence | | Medium density | Medium density | Medium density |
| Petiole pubescence | | Medium density | Medium density | Low density |
| Stipule length (mm) | Average | 35.74 | Not available | 21.96 |
| | Range | 30.2-39.7 | Not available | 19.92-24.58 |
| Stipule anthocyanin coloration | | Yes | Weak yes | Slight |
| Leaf margins | | Serrate to crenate | Commonly crenate | Crenate to serrate |
| Leaf color adaxial surface | | 364 U | 364 U | 371 U |
| Leaf color abaxial surface | | 363 U | 370 U | 7491 U |
| Petiole color | | 366 U | 383 U | 383 U |
| Leaf surface blistering | | Medium | Very weak | Slight |
| Leaf surface glossiness | | High | Medium | Moderate |

FLOWERS AND FRUIT

'Miss Jo' is a weak day neutral variety that has ever-bearing tendencies under certain temperature and horticultural conditions. This has been seen where plants grown in a coastal climate have continuously flowered throughout the growing season, while in nursery production in Manteca where summer temperatures are hot, some plants flower, while others do not. While 'Lucia' has longer inflorescences and 'Sweet Ann' has shorter inflorescences as compared to 'Miss Jo', when compared to their individual plant size all three varieties produce flowers that are at or above the canopy level, leaving flowers exposed to pollinators. The light red exterior color of the fruit of 'Miss Jo' is similar in color to that of 'Lucia' and 'Sweet Ann', however while 'Sweet Ann' often has an unripe shoulder, no such shoulder exists in fruit of 'Miss Jo' where it ripens nearly up to the calyx. The fruit of 'Miss Jo' has good culinary qualities including good conic shape, good size, lighter red color, and a sweet strawberry flavor.

In Table 3, comparative data for flower and fruit characteristics for 'Lucia', 'Sweet Ann' and 'Miss Jo' are set forth.

TABLE 3

Flower and Fruit Characteristics of 'Miss Jo' Compared to 'Lucia' and Sweet Ann'

| Characteristic | | Cultivar | | |
|---|---|---|---|---|
| | | 'Lucia' | 'Sweet Ann' | 'Miss Jo' |
| Petal number | | 5 | 5-6 | 5-8 |
| Petal length (mm) | Average | 12.44 | 11.21 | 11.37 |
| | Range | 10.6-14.3 | 9.2-13.13 | 10.16-12.51 |
| Petal width (mm) | Average | 11.86 | 11.05 | 10.84 |
| | Range | 10-13.1 | 9.0-13.1 | 9.23-12.15 |
| Position of flower (relative to foliage) | | most exposed | most exposed some even | most exposed some even |
| Pedicel length (mm) | Average | 430 | 330 | 372 |
| | Range | 380-540 | 240-420 | 329-435 |
| Sepal color (adaxial) | | 364 U | 364 U | 371 U |
| Sepal color (abaxial) | | 371 U | 370 U | 7491 U |
| Flower diameter (mm) | Average | 28.18 | 30.34 | 26.55 |
| | Range | 23.5-34.2 | 27.03-32.94 | 21.86-30.22 |

TABLE 3-continued

Flower and Fruit Characteristics of 'Miss Jo' Compared to 'Lucia' and Sweet Ann'

| Characteristic | Cultivar | | |
|---|---|---|---|
| | 'Lucia' | 'Sweet Ann' | 'Miss Jo' |
| Fruit color (external) | 1788 C | 185 C | 711 C |
| Fruit color (internal) | 179 C | 1788 C | 7417 U |

Leaf samples from 'Miss Jo', along with several proprietary selections from the breeding program including 'Lucia', 'Sweet Ann', 'Emilia' (U.S. Plant Pat. No. 30,427), 'Camila' (U.S. Plant Pat. No. 30,326), 'Ruby June' (U.S. Plant Pat. No. 27,190), 'Sangria' (U.S. Plant Pat. No. 30,426), 'Scarlet' (U.S. Plant Pat. No. 27,034), and 'Sierra' (U.S. Plant Pat. No. 33,284), were submitted to a lab for allelic fingerprint comparison to the over two hundred other varieties of strawberry in its data base. The allelic fingerprint analysis establishes that 'Miss Jo' is distinct and unique compared to the lab's large database of allelic fingerprints. While 'Miss Jo' has equivalent alleles to other varieties for some individual markers, when looked at with several markers, a unique fingerprint is established.

Table 4 below sets forth the test results of three markers.

TABLE 4

Allelic Fingerprint Analysis

| Cultivar | M1 | M2 | M3 |
|---|---|---|---|
| 'Camila' | 204, 206, 224, 229 | 190, 232 | 279, 281, 289 |
| 'Emilia' | 204, 206, 214, 229 | 190, 232 | 279, 281, 289 |
| 'Lucia' | 202, 204, 206, 229 | 188, 216, 232 | 279, 281, 289 |
| 'Ruby June' | 206, 224, 229 | 188, 190, 216, | 279, 289 |
| 'Sangria' | 204, 206, 229 | 190,216 | 279,289 |
| 'Scarlet' | 204, 206, 214, 229 | 173, 190, 232 | 279, 281, 289 |
| 'Sweet Ann' | 204, 206, 229 | 190, 216, 232 | 279, 281, 289 |
| 'Sierra' | 204, 206, 229 | 232 | 279, 289 |
| 'Miss Jo' | 204, 206, 214, 224, 229 | 190, 232, 263 | 279, 281, 289 |

We claim:

1. A new and distinct strawberry plant named 'Miss Jo' as described and illustrated by the characterizations set forth above.

* * * * *